(12) United States Patent
Janakat et al.

(10) Patent No.: US 7,938,338 B2
(45) Date of Patent: May 10, 2011

(54) AIR FRESHENER APPARATUS

(76) Inventors: Omar Janakat, East Rutherford, NJ (US); Cheryl Palko, Butler, NJ (US)

( * ) Notice: Subject to any disclaimer, the term of this patent is extended or adjusted under 35 U.S.C. 154(b) by 197 days.

(21) Appl. No.: 12/181,895

(22) Filed: Jul. 29, 2008

(65) Prior Publication Data

US 2009/0114736 A1    May 7, 2009

Related U.S. Application Data

(60) Provisional application No. 60/984,487, filed on Nov. 1, 2007.

(51) Int. Cl.
*A24F 25/00* (2006.01)
(52) U.S. Cl. ............................................. 239/44; 239/58
(58) Field of Classification Search ............... 239/34–36, 239/44, 47, 49, 51.5, 55, 57–59
See application file for complete search history.

(56) References Cited

U.S. PATENT DOCUMENTS

| | | | | |
|---|---|---|---|---|
| 4,065,261 A * | 12/1977 | Fukada | ............................. | 261/95 |
| 5,342,584 A * | 8/1994 | Fritz et al. | ....................... | 422/124 |
| 6,481,639 B1 * | 11/2002 | Pozzo | ............................... | 239/47 |
| 7,140,553 B2 * | 11/2006 | Zobele | ............................. | 239/34 |
| 7,204,870 B2 * | 4/2007 | Zobele et al. | .................... | 96/222 |
| 2005/0224595 A1 * | 10/2005 | Kuiper | ............................ | 239/59 |

* cited by examiner

*Primary Examiner* — Davis Hwu
(74) *Attorney, Agent, or Firm* — Jerry Haynes; Law Offices of Jerry D. Haynes, P.A.

(57) ABSTRACT

Disclosed is an air freshener apparatus capable of being attached to an air-vent for receiving air. The air freshener apparatus comprises an enclosure formed by a front portion and a back portion. The enclosure removably secures a reservoir having an aromatic substance. Further, an attaching member extends from the back portion to attach the enclosure to the air-vent. Furthermore, an air-vent opening is configured on the back portion for receiving the air from the air-vent on removably attaching the enclosure to the air-vent, and further, directing the air to the reservoir for obtaining a mixture of the air and the aromatic substance. Furthermore, an adjustable opening is configured on the front portion for dispensing the mixture out of the enclosure. Moreover, a regulating means is provided for adjusting the adjustable opening for dispensing required amount of the mixture therefrom, and a lighting member is provided for illumination purpose.

6 Claims, 2 Drawing Sheets

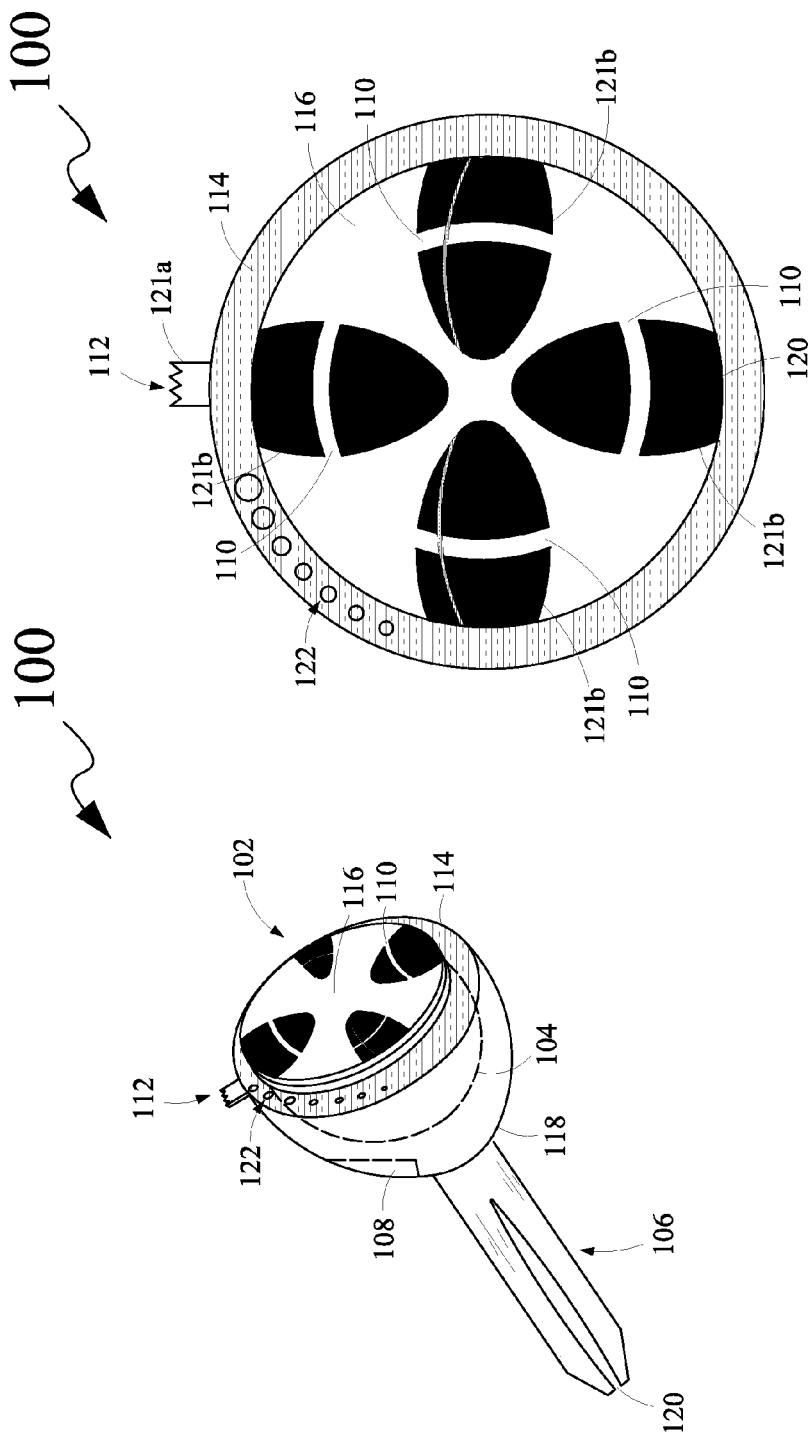

AIR FRESHENER APPARATUS

CROSS-REFERENCE TO RELATED APPLICATIONS

The present invention claims priority under 35 United States Code, Section 119 on the U.S. Provisional Patent Application numbered 60/984,487, filed on Nov. 1, 2007, the disclosure of which is incorporated by reference.

FIELD OF THE INVENTION

The present invention relates to an air freshener apparatus, and more particularly, to a luminescent air freshener apparatus that may be used in an automobile.

BACKGROUND OF THE INVENTION

Due in part to an enclosed nature of an automobile cabin, there is a need to control the environment within the cabin to minimize unpleasant odors. Various apparatuses are known in the art for minimizing these odors. One of such apparatus includes a cardboard structure that is scented. Typically, such an apparatus may be removably hanged from an automobile's rear-view mirror. The hanged apparatus may dispense scent to minimize unpleasant odors in the automobile cabin. However, conventional apparatuses are lacking in their ability to hold and dispense aromatic odor for a long duration, and therefore do not permit sustained use. Further, such conventional apparatuses may also interfere with a field of vision of a driver of the automobile due to the installation on the rear-view mirror.

Furthermore, such conventional apparatuses do not permit a user to adjust rate or intensity at which the scent emanates therefrom. Thus the conventional apparatuses are not able to adopt different environmental conditions in the automobile cabin. Also, the conventional apparatuses because of their structural configuration are not capable of enhancing aesthetic look of the environment, wherever installed.

Accordingly, there exists a need for an apparatus that is capable of varying flow or intensity of a scent in order to adopt different environmental conditions in an automobile cabin. Furthermore, there exists need for an apparatus capable of increasing aesthetic look of the environment, wherever installed.

SUMMARY OF THE INVENTION

In view of the forgoing disadvantages inherent in the prior art, the general purpose of the present invention is to provide an air freshener apparatus that is configured to include all advantages of the prior art, and to overcome the drawbacks inherent in the prior art.

An object of the present invention is to provide an air freshener apparatus that is capable of varying a flow rate or intensity of an aromatic substance disposed therein in order to adopt different environmental conditions in an automobile cabin, and enabling the air freshener apparatus to work for a longer duration.

Another object of the present invention is to provide an air freshener apparatus that is capable of illuminating light therefrom for visualization of the level of a scent therein, and for enhancing aesthetic look of the air freshener apparatus, thereby increasing aesthetic look of an environment.

To achieve the above objects, in an aspect of the present invention, an air freshener apparatus is provided. The air freshener apparatus is capable of being attached to an air-vent for receiving air. The air freshener apparatus comprises an enclosure having a front portion and a back portion, a reservoir having an aromatic substance therein, an attaching member, at least one air-vent opening, at least one adjustable opening, a regulating means, and a lighting member. More particularly, the enclosure is capable of removably securing the reservoir therewithin. Further, the attaching member is extending from the back portion of the enclosure removably attaching the enclosure to the air-vent. Furthermore, the at least one air-vent opening is configured on the back portion of the enclosure for receiving the air from the air-vent, and directing the air to the reservoir for obtaining a mixture of the air and the aromatic substance. Furthermore, the at least one adjustable opening is configured on the front portion of the enclosure for dispensing the mixture therefrom. Moreover, the regulating means is adjustably disposed on at least one of the back portion and the front portion. The regulating means is capable of being regulated for adjusting the at least one adjustable opening for dispensing required amount of the mixture therefrom. Also, the lighting member is disposed on the front portion of the enclosure for being illuminated to visualize a position of the regulating means for adjusting the at least one adjustable opening for dispensing the required amount of the mixture.

Further, in an aspect of the present invention, an air freshener apparatus package is provided for packaging an air freshener apparatus therein. The air freshener apparatus package comprises a packaging enclosure and a sniffing arrangement. The sniffing arrangement is pasted on the packaging enclosure that is capable of being scratched to sniff an aromatic substance for facilitating a buyer to buy the air freshener apparatus of a desired aroma.

These together with the other aspects of the present invention, along with the various features of novelty that characterized the present invention, are pointed out with particularity in the claims annexed hereto and form a part of the present invention. For a better understanding of the present invention, its operating advantages, and the specified object attained by its uses, reference should be made to the accompanying drawings and descriptive matter in which there are illustrated exemplary embodiments of the present invention.

BRIEF DESCRIPTION OF THE DRAWINGS

The advantages and features of the present invention will become better understood with reference to the following detailed description and claims taken in conjunction with the accompanying drawings, wherein like elements are identified with like symbols, and in which:

FIG. 1 illustrates a perspective view of an air freshener apparatus, in accordance with an exemplary embodiment of the present invention;

FIG. 2 illustrates a front view of the air freshener apparatus of FIG. 1; and

Like reference numerals refer to like parts throughout the description of several views of the drawings.

DETAILED DESCRIPTION OF THE INVENTION

Figure 3:
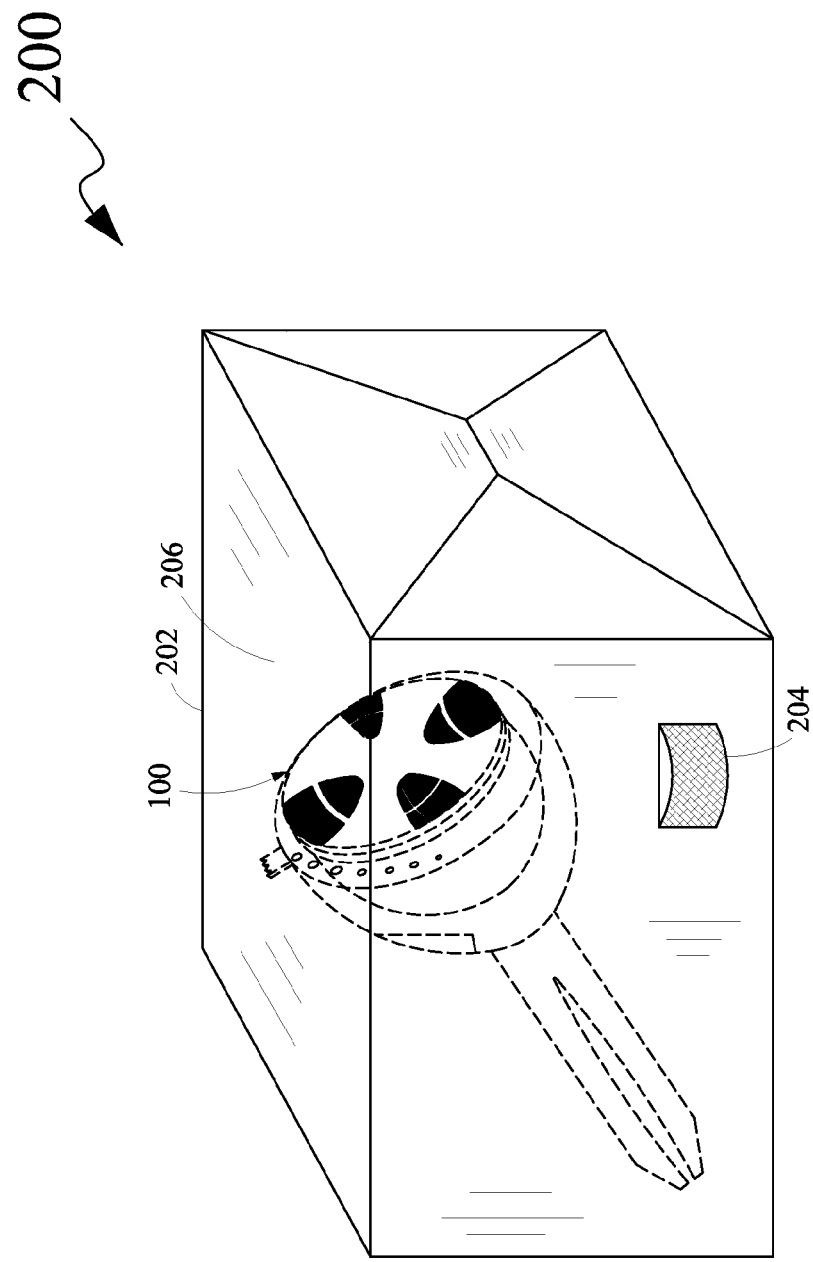
FIG. 3 illustrates a perspective view of an air freshener apparatus package, in accordance with an exemplary embodiment of the present invention.

For a thorough understanding of the present invention, reference is to be made to the following detailed description, including the appended claims, in connection with the above-described drawings. Although the present invention is described in connection with exemplary embodiments, the present invention is not intended to be limited to the specific forms set forth herein. It is understood that various omissions and substitutions of equivalents are contemplated as circumstances may suggest or render expedient, but these are intended to cover the application or implementation without departing from the spirit or scope of the claims of the present invention. Also, it is to be understood that the phraseology and terminology used herein is for the purpose of description and should not be regarded as limiting.

The term "front", "back" and the like, herein do not denote any order, elevation or importance, but rather are used to distinguish placement of one element over another, and the terms "a" and "an" herein do not denote a limitation of quantity, but rather denote the presence of at least one of the referenced item.

The present invention provides an air freshener apparatus capable of being attached to an air-vent for receiving air. The air freshener apparatus includes an aromatic substance that mixes with the air to obtain a mixture thereof. Further, the mixture is dispensed from the air freshener apparatus for minimizing unpleasant odors in a closed cabin. The air freshener apparatus of the present invention may be used in an automobile for minimizing unpleasant odors in an automobile cabin. It is envisioned that the present invention can be easily incorporated into a multitude of utility and at a multitude of places which includes but is not limited to, homes, and commercial places such as offices, restaurants, hotels, fast food places, and the like. Also, the air freshener apparatus enhances aesthetic look of the closed cabin, wherever installed.

Referring now to FIGS. 1 and 2 an air freshener apparatus 100 is shown, according to an exemplary embodiment of the present invention. The air freshener apparatus 100 is capable of being attached to an air-vent (not shown) for receiving air. In one embodiment of the present invention, the air freshener apparatus 100 is capable of being attached to an air-vent (not shown) of an automobile (not shown) for receiving air. The air freshener apparatus 100 comprises an enclosure 102, a reservoir 104, an attaching member 106, at least one air-vent opening, such as an air-vent opening 108, at least one adjustable opening 110, a regulating means 112 and a lighting member 114.

More particularly, the enclosure 102 includes a front portion 116 and a back portion 118. In one embodiment, the front portion 116 and the back portion 118 configure to form a hemispherical shaped enclosure. Preferably, the front portion 116 is flat and the back portion 118 is hemispherical in shape to obtain the hemispherical shaped enclosure. Further, the reservoir 104 is capable of storing and dispensing an aromatic substance (not shown) therefrom. The reservoir 104 storing the aromatic substance is removably secured within the enclosure 102. More particularly, in one embodiment, the reservoir 104 partially receives a dispensing stick (not shown) therein. The dispensing stick is capable of drawing up the aromatic substance from storage in the reservoir 104. Without departing the scope of the present invention, in one embodiment, the dispensing stick may be made of cotton material of rising-up the aromatic substance stored in the reservoir 104. Further, the reservoir 104 is capable of being replaced by a new reservoir similar to the reservoir 104 after the aromatic substance present within the reservoir 104 is exhausted. In one embodiment, the aromatic substance may be of made at least one of oils, perfumes and waxes.

Further, the attaching member 106 (see FIG. 1) extending from the back portion 118 of the enclosure 102 is capable of removably attaching the enclosure 102 with the air-vent of the automobile. In one embodiment, the attaching member 106 is of oblong shape. More particularly, the attaching member 106 has a plurality of branched members 120 that expand to removably attach with the air-vent of the automobile, thereby attaching the air freshener apparatus 100 with the air-vent of the automobile. In the present embodiment, attachment of the air freshener apparatus 100 with the air-vent of the automobile has been presented for purpose of understanding and description, however, it will be evident to a person skilled in the art that the air freshener apparatus 100 may be attached to an air-vent, other than the air-vent of the automobile. Furthermore, the air-vent opening 108 is configured on the back portion 118 of the enclosure 102. The air-vent opening 108 is capable of receiving the air from the air-vent of the automobile, and directing the air to the reservoir 104. Upon receiving the air for the air-vent, the aromatic substance that has been raised-up from the reservoir 104 by the dispensing stick is mixed with the air for obtaining a mixture of the air and the aromatic substance.

The at least one adjustable opening, which is shown to include four adjustable openings 110 in FIGS. 1 and 2. The adjustable openings 110 are configured on the front portion 116 of the enclosure 102 for being adjusted to dispense the mixture therefrom for freshening an inner space of the automobile.

Further, the regulating means 112 is adjustably disposed on at least one of the front portion 116 and the back portion 118 of the enclosure 102. Without departing from the scope of the present invention, the regulating means 112, according to an exemplary embodiment, is disposed on the front portion 116 of the air freshener apparatus 100 as shown in FIGS. 1 and 2. In one embodiment, the regulating means 112 includes a knob 112a that may regulate the regulating means 112 to adjustably cover the adjustable openings 110. More particularly, the regulating means 112, for adjustably covering the adjustable openings 110, includes flaps 112b disposed on the corresponding adjustable openings 110. The flaps 112b may be regulated by the knob 112a for adjusting corresponding openings of the adjustable openings 110. Taking into consideration different environmental conditions, such as a bigger inner space of the automobile or a smaller inner space of the automobile, positions of the flaps 112b disposed on the corresponding adjustable opening 110, may be adjusted to dispense required amount of the aromatic substance from the reservoir 104, thereby preventing undesirable amount of the aromatic substance from being dispensed out of the reservoir 104.

In one embodiment of the present invention, a readable gauge 122 is provided on the front portion 116 of the enclosure 102 for facilitating the user to read position of the flaps 112b in order to determine a level of opening of the adjustable openings 110. More particularly, the readable gauge 122 is a dotted light meter that indicates minimum to maximum value of the position of the flaps 112b. The user may adjust the flaps 112b in-between the minimum to the maximum value on looking at the position of the readable gauge 122, for obtaining required opening of the adjustable openings 110 in order to dispense a required amount of the aromatic substance out of the reservoir 104. The readable gauge 122 is capable of illuminating light therefrom to facilitate the user to adjust the adjustable openings 110 in-between the minimum to the maximum value in dark. Apart from the readable gauge 122, the lighting member 114 is disposed on the front portion 116 of the enclosure 102.

Importantly, the lighting member 114 is capable of being illuminated to be used by a user for visualizing the position of the regulating means 112 in dark. The user, upon visualizing, may adjust the opening of the adjusting openings 110 for dispensing the required amount of the mixture of the aromatic substance and the air, in the dark. Apart from visualizing the position of the regulating means 112 in dark, the lighting member 114 may enhance aesthetic look of the air freshener apparatus 100, thereby providing a decorative air freshener apparatus. Without departing the scope of the present invention, in an embodiment, the lighting member 114 may be a neon tube. In another embodiment of the present invention, the lighting member 114 may be fluorescent light tube.

Furthermore, the air freshener apparatus 100 may include a power source (not shown) for powering the lighting member 114 for illumination. In an embodiment, the power source may be a battery pack (not shown) detachable secured on the air freshener apparatus 100. Without departing from the scope of the present invention, when the air freshener apparatus 100 is used in the automobile, the power source may be an automobile cigarette lighter arrangement (not shown). The automobile cigarette lighter arrangement may supply required power to the lighting member 114 for illumination. Further, the air freshener apparatus 100 may include a switching mechanism (not shown) for switching 'on' and switching 'off' the power source.

Furthermore, in an embodiment, the air freshener apparatus 100 may include a heating member (not shown) disposed on the reservoir 104 for heating the aromatic substance. Heating member may be heated by the power source for agitating and dispensing the aromatic substance from the reservoir 104.

Referring now to FIG. 3, an air freshener apparatus package 200 is shown, according to an exemplary embodiment of the present invention. The air freshener apparatus 200 is capable of accommodating an air freshener apparatus, such as the air freshener apparatus 100. In an embodiment, the air freshener apparatus package 200 comprises the air freshener apparatus 100, a packaging enclosure 202 and a sniffing arrangement 204. The packaging enclosure 202 has an inner space 206 for accommodating the air freshener apparatus 100 therein. The sniffing arrangement 204 is pasted on the packaging enclosure 202 by means of an adhesive element (not shown). The sniffing arrangement 204 is capable of being scratched by a buyer to sniff a type of the aromatic substance in the air freshener apparatus 100. The sniffing arrangement 204 facilitates a buyer to buy the air freshener apparatus 100 of a desired aroma by knowing type of the aromatic substance. The sniffing arrangement 204 enables the buyer to select the air freshener apparatus of desired aroma without opening the packaging enclosure 202.

The air freshener apparatus 100 of the present invention provide following advantages. The air freshener apparatus 100 is capable of varying a flow rate or intensity of an aromatic substance disposed therein in order to adopt different environmental conditions in an automobile cabin, and enabling the air freshener apparatus to work for a longer duration. The air freshener apparatus 100 is capable being illuminated for visualization of the level of an aromatic substance therein. Also, the illumination enhance aesthetic look of the air freshener apparatus 100, thereby increasing aesthetic look of an environment, wherever the air freshener apparatus 100 is installed.

The foregoing descriptions of specific embodiments of the present invention have been presented for purposes of illustration and description. They are not intended to be exhaustive or to limit the present invention to the precise forms disclosed, and obviously many modifications and variations are possible in light of the above teaching. The embodiments were chosen and described in order to best explain the principles of the present invention and its practical application, to thereby enable others skilled in the art to best utilize the present invention and various embodiments with various modifications as are suited to the particular use contemplated. It is understood that various omission and substitutions of equivalents are contemplated as circumstance may suggest or render expedient, but such are intended to cover the application or implementation without departing from the spirit or scope of the claims of the present invention.

What is claimed is:

1. An air freshener apparatus capable of being attached to an air-vent for retrieving air, the air freshener apparatus comprising:
   an enclosure having a front portion and a back portion;
   a reservoir having an aromic substance, the reservoir removably secured within the enclosure;
   an attaching member extending from the back portion of the enclosure, the attachment member capable of removably attaching the enclosure to the air-vent;
   at least one air-vent opening configured on the back portion of the enclosure for receiving the air from the air-vent, and directing the air to the reservoir for obtaining a mixture of the air and the aromatic substance;
   at least one adjustable opening configured on the front portion of the enclosure, with at least one adjustable opening capable of being adjusted for dispensing the mixture therefrom;
   a regulating means adjustably disposed on at least one of the front portion and the back portion the regulating means being capable of being regulated for adjusting the at least one adjustable opening for dispensing required amount of mixture therefrom;
   a lighting member disposed around the perimeter of the front portion of the enclosure, the lighting member capable of being illuminated to visualize a position of the regulating means for adjusting the at least one adjustable opening for dispensing the required amount of the mixture; and
   a readable gauge configured on the front portion of the enclosure for facilitating a user to read a position of the regulating means, where the readable gauge is a dotted meter that indicates minimum to maximum value, where the lighting member provides a background for the readable gauge.

2. The air freshener apparatus of claim 1, wherein the reservoir further comprises a dispensing stick, the dispensing stick is partially disposed in the reservoir for rising-up the aromatic substance from the reservoir.

3. The air freshener apparatus of claim 1, further comprising a power source for powering the lighting member for illumination.

4. The air freshener apparatus of claim 1, further comprising a switching mechanism for switching on and switching off the power source.

5. The air freshener apparatus of claim 1, wherein the lighting member is a neon tube.

6. The air freshener apparatus of claim 1, wherein the aromatic substance is made of at least one of oils, perfumes and waxes.

* * * * *